United States Patent
Burnham

(10) Patent No.: US 11,345,611 B2
(45) Date of Patent: May 31, 2022

(54) SWIMMING POOL WATER MONITORING DEVICE AND METHOD

(71) Applicant: Damar Supplies Limited, Birstall (GB)

(72) Inventor: Douglas Burnham, Leeds (GB)

(73) Assignee: DAMAR SUPPLIES LIMITED, Birstall (GB)

( * ) Notice: Subject to any disclaimer, the term of this patent is extended or adjusted under 35 U.S.C. 154(b) by 60 days.

(21) Appl. No.: 16/605,294

(22) PCT Filed: Apr. 19, 2018

(86) PCT No.: PCT/GB2018/051037
§ 371 (c)(1),
(2) Date: Oct. 15, 2019

(87) PCT Pub. No.: WO2018/193263
PCT Pub. Date: Oct. 25, 2018

(65) Prior Publication Data
US 2021/0147255 A1    May 20, 2021

(30) Foreign Application Priority Data
Apr. 19, 2017 (GB) .................................. 1706168

(51) Int. Cl.
*C02F 1/00* (2006.01)
*C02F 9/00* (2006.01)
(Continued)

(52) U.S. Cl.
CPC ............... *C02F 1/008* (2013.01); *C02F 9/00* (2013.01); *E04H 4/1209* (2013.01); *E04H 4/129* (2013.01);
(Continued)

(58) Field of Classification Search
CPC ...... C02F 1/008; C02F 9/00; C02F 2201/009; C02F 1/685; C02F 2209/008;
(Continued)

(56) References Cited

U.S. PATENT DOCUMENTS 3,837,016 A * 9/1974 Schindler ................ E04H 4/129
4/489
4,206,522 A * 6/1980 Baker .................... E04H 4/1227
210/105
(Continued)

FOREIGN PATENT DOCUMENTS

EP      2247807 A1    11/2010
EP      2247807 B1     7/2016
WO   2018/193263 A1   10/2018

OTHER PUBLICATIONS

International Search Report for International application No. PCT/GB2018/051037; dated Jul. 10, 2018; 4 pages.

*Primary Examiner* — Fred Prince
(74) *Attorney, Agent, or Firm* — Shumaker, Loop & Kendrick, LLP

(57) ABSTRACT

There is described a water monitoring device for monitoring a body of water. The body of water comprises a main body of water and a water inlet and/or water outlet. The water monitoring device comprises a sensor operable to generate data in relation to a property of the body of water, an attachment member operable to removably arrange the device in a substantially stationary position adjacent to the water inlet and/or water outlet of the body of water; and a communication member operable to transmit the data relating to a property of the body of water to a remote device. Also described is a water monitoring apparatus and a method of monitoring a body of water.

18 Claims, 5 Drawing Sheets

(51) Int. Cl.
*E04H 4/12* (2006.01)
*E04H 4/14* (2006.01)
*E04H 4/16* (2006.01)
*G01N 33/18* (2006.01)
*C02F 1/40* (2006.01)
*C02F 1/68* (2006.01)
*C02F 103/42* (2006.01)

(52) U.S. Cl.
CPC ............ *E04H 4/1281* (2013.01); *E04H 4/148* (2013.01); *E04H 4/1654* (2013.01); *G01N 33/18* (2013.01); *C02F 1/001* (2013.01); *C02F 1/40* (2013.01); *C02F 1/685* (2013.01); *C02F 2103/42* (2013.01); *C02F 2201/009* (2013.01); *C02F 2209/008* (2013.01); *C02F 2209/02* (2013.01); *C02F 2209/29* (2013.01)

(58) Field of Classification Search
CPC ........ C02F 2209/29; C02F 1/001; C02F 1/40; C02F 2103/42; C02F 2209/02; E04H 4/148; E04H 4/1281; E04H 4/1209; E04H 4/129; E04H 4/1654; G01N 33/18

USPC ........ 210/143, 167.11, 167.1, 739, 742, 744, 210/754
See application file for complete search history.

(56) References Cited

U.S. PATENT DOCUMENTS

| | | | |
|---|---|---|---|
| 5,314,589 A | * | 5/1994 | Hawley ................. C02F 1/4674 205/618 |
| 6,792,956 B2 | * | 9/2004 | Bredo ................... E04H 4/1654 134/10 |
| 10,024,578 B1 | * | 7/2018 | Rutkai .................... E04H 4/129 |
| 2001/0045380 A1 | * | 11/2001 | Khan ...................... C02F 1/008 210/85 |
| 2006/0104720 A1 | | 5/2006 | Haski et al. |
| 2007/0160498 A1 | | 7/2007 | Biberger |
| 2013/0175802 A1 | | 7/2013 | Breau et al. |
| 2017/0349454 A1 | * | 12/2017 | Cai ........................ C02F 1/444 |

* cited by examiner

SWIMMING POOL WATER MONITORING DEVICE AND METHOD

CROSS REFERENCE TO RELATED PATENT APPLICATIONS

This application claims the benefit of and priority to PCT/GB2018/051037 filed Apr. 19, 2018 which claims the benefit of and priority to Great Britain Application No. 1706168.0 filed on Apr. 19, 2017.

TECHNICAL FIELD AND BACKGROUND OF THE INVENTION

The present invention relates to a water monitoring device. More specifically, the present invention relates to a water monitoring device for monitoring a body of water, in particular, for monitoring swimming pools. The invention also extends to a water management apparatus including the water monitoring device.

Bodies of water, such as swimming pools, can require regular maintenance in order to preserve appropriate conditions. It is desirable to be able to determine that properties such as water temperature, chemical levels, pH, pool cover performance and lighting performance are within the necessary parameters. If one or more of these properties is found to be above or below the appropriate levels then it may also be necessary to adjust the devices that control the property.

Known water testing or monitoring systems include hand held devices that are inserted into the body of water to measure one or more property of the water. Such systems however require that the user is in proximity of the body of water and provides limited information that is correct only at the point of use. These known testing or monitoring systems typically only monitor basic water conditions and do not monitor, for example, filter, pump or heater efficiency or pool occupancy etc.

Therefore, there is a requirement for an improved water monitoring system. It is an object of aspects of the present invention to provide one or more solutions to the above mentioned or other problems.

BRIEF SUMMARY OF THE INVENTION

According to a first aspect of the present invention there is provided a water monitoring device for monitoring a body of water, the body of water comprising a main body of water and a water inlet and/or water outlet, the water monitoring device comprising:
  a sensor operable to generate data in relation to a property of the body of water;
  an attachment member operable to removably arrange the device in a substantially stationary position adjacent to the water inlet and/or water outlet of the body of water; and
  a communication member operable to transmit the data relating to a property of the body of water to a remote device.

According to a second aspect of the present invention there is provided a swimming pool water inlet and/or water outlet assembly, the assembly comprising a water monitoring device according to the first aspect of the present invention.

According to a third aspect of the present invention there is provided water management apparatus for monitoring and managing properties of a body of water comprising a main body of water and a water inlet and/or water outlet, the water management apparatus comprising:
  a water monitoring device according to the first aspect of the present invention; at least one treatment member operable to effect a change in a property of the body of water.

According to a fourth aspect of the present invention, there is provided a kit of parts for a water monitoring system, comprising
  a water monitoring device according to the first aspect of the present invention; and
  at least one treatment member operable to effect a change in a property of the body of water.

According to a fifth aspect of the present invention, there is provided a swimming pool comprising a water monitoring device according to the first aspect of the present invention, a swimming pool water inlet and/or water outlet assembly according to the second aspect of the present invention or a water management apparatus according to the third aspect of the present invention.

According to a sixth aspect of the present invention, there is provided a method of monitoring a body of water, and optionally managing a property of the body of water, the body of water comprising a main body of water and a water inlet and/or water outlet, the method comprising:
  (a) attaching a water monitoring device according to the first aspect of the present invention in a substantially stationary position adjacent to the water inlet and/or water outlet of the body of water;
  (b) generating data in relation to a property of the body of water;
  (c) communicating the data to a remote device;
  (d) optionally, sending an instruction from the remote device to a water treatment member that is operable to effect a change in the property of the body of water.

DETAILED DESCRIPTION OF THE INVENTION

The body of water may be contained in any suitable system. For example, the body of water may be the water in a pond, a lake, a fountain, a hot tub, a spa or a swimming pool (indoor or outdoor). Preferably, the body of water is the water in a swimming pool system. In one embodiment, therefore, the water monitoring device may be a water monitoring device for monitoring a swimming pool.

The sensor of the present invention may be operable to detect any suitable property of the body of water. For example, the sensor may be operable to detect the chemical levels in the body of water, such as the chlorine content, the pH, the mineral content, the presence of microorganisms; or a combination thereof. The sensor may additionally/alternatively be operable to detect physical aspects of the body of water, for example the temperature; the water level; the flow speed; clarity; or a combination thereof. The sensor may additionally/alternatively be operable to directly detect the performance of treatment members such as functioning of the pool cover, occupancy of the body of water, ozone generation; whether lights are in an on or off state; or a combination thereof.

The present invention may comprise two or more sensors, suitably, the water monitoring device comprises two or more sensors. Preferably, the device comprises a first sensor operable to generate data in relation to a property of the main body of water and a second sensor operable to generate data in relation to a property of the water at the inlet/outlet, more preferably the first and second sensor are operable to generate data in relation to the same property, for example the temperature of the water in the main body and the temperature of the water at the inlet/outlet. Accordingly, the difference between the desired property in the water at the inlet/outlet and the main body of water can be detected.

It is an advantage of the present invention that when the water monitoring device comprises a sensor which, in use, is arranged to monitor water at the inlet/outlet and also a sensor arranged to monitor the main body of water, the data collection is improved. For example, data can be collected from the relatively small sample of water that has recently been exposed to treatment members such as, for example, filters, pumps and heaters etc., as well collecting data from the main body of water. Thus, the monitoring device can measure both the property in the main body of water and the property in the water that is being fed into the main body of water. This enables changes to be detected more quickly than would typically be expected because in prior art systems the properties would need to dissipate to and through the main body of water before a change could be identified.

The sensor may comprise an optical module such as a camera. Suitably, the device comprises an optical module operable to generate an image of the water inlet/outlet channel. Advantageously, an optical module in the inlet/outlet channel enables the user to monitor the amount of bubbles in the flow. If there are excessive bubbles within the water flow it may indicate problems with the pool circulatory system such as air leaks into a suction manifold. Such problems unaddressed can lead to a pool flow or de-priming of pumps.

The sensor may comprise a hydro-sonic module operable to detect sound waves in the main body of water. Advantageously, a hydro-sonic module can detect the presence of intrusions into the pool.

The sensor may comprise a spectroscopy module operable to generate date in relation to the chemical composition of the water, such as chlorine content, pH, microorganism and/or the mineral content of the water.

The sensor may comprise an optical transmitter and receiver, such as a laser transmitter and receiver. Suitably, the optical transmitter is operable to project light toward the surface of the body of water in use and the receiver is operable to collect light extending downwardly from the surface of the water. Preferably, the receiver is operable to collect light that has been emitted by the transmitter and reflected by the water. Advantageously, the data collected by the aforementioned transmitter and receiver may be used to determine the water level of a body of water and also whether a cover is correctly in place over the surface of the water, depending on the amount of light that is collected by the receiver and the time taken for light to be transmitted from the device and returned to the device. Sonic-based transmitters and receivers device may additionally/alternatively be used to generate data for cover and/or surface water level detection, as may a pressure sensitive sensor operable to measure the head of water above the device.

A suitable sonic sensor may be Maxbotix MB 7077 made waterproof using a sealant and calibrated for water according to the methods well known in the field.

It is important to know the water level in, for example, a swimming pool or spa. If the water level is not at the correct operating level, significant problems can occur. The correct water level is essential to the efficient operation of such as, filtration systems and pump flow. If the water level is too low, the circulating pump may not prime fully or it may stop circulating the water. This would render other equipment un-operational, such as, heating and chemical dosing which require good circulation of pool water. Furthermore, treatment members such as automatic pool surface cover systems are also water level critical for 'non jamming' operation. If the water level is too high or too low then the cover may jam. This can cause serious damage to the cover equipment. Advantageously, the present invention allows for the water level and cover operation to be measured and sent to a remote device, providing the user with an easy method of measuring the water level and an early warning of malfunction.

The sensor may comprise a flow detection module, the flow detection module may comprise pressure sensors and/or movable blades. Such a flow detection sensor may comprise a generator operable to generate a voltage or a plurality of pulses by rotation of the blades as the water passes over the blades. The water monitoring device may be operable to generate data in relation to the voltage output or number of pulses of the generator. Said data may be used to calculate the flow speed of the body of water, suitably at the water inlet/outlet. Optionally, should a battery be present the electrical output may be operable to charge the battery. This charging function can reduce the requirement for removing the device, assembly or apparatus from the body of water.

Pulses may be generated by including a component operable to perform "Hall effect" magnetic switching, whereby the component comprises a counting device operable to send a control signal to a magnetically operated switch that is open or closed when in close proximity to a magnet. Optionally such a magnet may be fitted to a blade that on rotation switches the "hall effect" operable switch to open/close at a rate proportional to its rotational speed.

The device and/or assembly of the present invention may further comprise one or more treatment members operable to effect a change in a property of the body of water. The treatment members of the apparatus and/or kit of parts of the present invention, and/or optionally the device and/or the assembly may be selected from one or more of a light source; a heater such as a water heating element; a chemical dosing member, such as a salt generator, a chlorinator, an ionizer; a water cooling element; a hydro-sonic device; a laser light projecting device; an ozone generator; an audible alarm, a pump, a filter, a cover, a robotic cleaner or combinations thereof. Such devices will be known to a person skilled in the art.

Preferably, the treatment members are in the form of an ancillary device that is remote from the water monitoring device but arranged such as to interact with the body of water. Preferably, one or more of the treatment members devices are operable to receive data from, and optionally send data to, the water monitoring device and/or the remote device.

A hydro-sonic device may be used to, for example, generate and/or transmit sound waves through the body of water such that a user/swimmer may audibly detect the transmitted data. For example, the data transmitted may be music and/or entertainment.

A light projecting device may be used to, for example, create visual images within the body of water such that a user/swimmer may visually detect the images. For example, the visual images may be holographic or generated on the side walls and/or the bottom floor of the body of water, such as a swimming pool, and may provide status information and/or alerts or entertainment.

A treatment member may comprise a device operable to give a visual indication when a detected property of the body of water is non-optimal. The term "non-optimal" is as hereinbefore defined. The visual indicator may be any suitable indicator. For example, the visual indicator may be operable to indicate if the body of water, such as a swimming pool, is safe to use or unsafe to use. Additionally or alternatively, the visual indicator may be operable to indicate if an treatment member or sensor is functioning. The visual indicator may comprise any suitable means. For example, the visual indicator may be a light, such as an LED light, and array of LEDs, a clear white light, a coloured light or the like. Advantageously, the use of a visual indicator may allow a user to receive information regarding the properties of the body of water when on site, i.e. when in or around the body of water. The visual indicator treatment member, when present, may be located at any suitable location. For example, the visual indicator may be attached to or may be integral with the water monitoring device or may be located at a different position within the body of water, such as a swimming pool.

The water monitoring device according to any aspect of the present invention may comprise an attachment member operable to removably attach the device in a substantially stationary position adjacent to the water inlet and/or water outlet of the body of water, such as a swimming pool. Suitably the attachment member is operable to hold the water monitoring device in fluid communication with the inlet/outlet such that water passing from the inlet/outlet passes through the device before entering the main body of water.

Positioning the water monitoring system of adjacent to a water inlet and/or water outlet of the body of water, such as a swimming pool, is the most appropriate location, providing more information with regard to the properties of the body of water than can be obtained by devices of the prior art such as mobile/hand held devices or fully installed devices.

The attachment member may be operable to removably attach the device in a substantially stationary position adjacent to one or more end(s) of a water inlet and/or water outlet. For example, the attachment member may be operable to removably attach the device in a substantially stationary position adjacent to a water inlet and/or water outlet on the inside and or outside of the body of water, such as a swimming pool. For the avoidance of doubt, by the term "inside of the body of water" and like terms as used herein is meant that the water monitoring device is located within the space defined by the side walls and the bottom floor of the pool. By the term "outside of the body of water" and like terms as used herein is meant that the water monitoring device is located outside of the space defined by the side walls and the bottom floor of the pool. The attachment member may be operable to removably attach the water monitoring device above or below the water level of the water in the body of water, such as a swimming pool. Preferably, the attachment member may be operable to removably attach the water monitoring device below the water level of the water in the body of water, such as a swimming pool. Suitably, the attachment member may be operable to allow the water monitoring device to be removably attached below the water level by an adaptor that may be positioned on and/or fixed to the edge of the body of water such that the sensors etc. are positioned below the water level.

The attachment member may comprise any suitable attachment means. Suitably, the attachment member may comprise nails, screws or the like, may comprise a 'snap fit mechanism', or may comprise a threaded region operable to threadedly engage with a threaded region of a water inlet and/or water outlet of the body of water, such as a swimming pool.

Suitably, the water monitoring device of the present invention may be operable to be retrofitted to a water inlet and/or water outlet of the body of water, such as a swimming pool. Preferably, the water monitoring device may be adapted to fit to a water inlet and/or water outlet of the body of water, such as a swimming pool, whereby the adaption means allows for easy fitting of the device, fixing of the device and/or removal of the device. For example, the attachment member may comprise a threaded region operable to threadedly engage with a threaded region of a water inlet and/or water outlet of the body of water, such as a swimming pool.

Preferably, the attachment member of the water monitoring device may be operable to allow the device to be removably attached to an insert of a water inlet and/or water outlet of the body of water, such as a swimming pool. The water monitoring device may be operable to be removably attached an insert of a water inlet and/or water outlet of the body of water by any suitable means. For example, the attachment member may comprise a threaded region operable to threadedly engage with a threaded region of an insert of a water inlet and/or water outlet of the body of water, such as a swimming pool.

In certain embodiments, the attachment means may allow a 'plug and play' type fixing arrangement to a water inlet and/or water outlet of the body of water, such as a swimming pool, allowing for remote charging or changing and/or service and/or repair of the device.

The water monitoring device may optionally further comprise a locking mechanism operable to allow the device to be locked in position with respect to a water inlet and/or water outlet of the body of water until such time that the locking mechanism is released. Suitably, the locking mechanism may be employed to fix or lock the water monitoring device in a particular orientation in relation to the water inlet and/or water outlet of the body of water, such as a swimming pool. Advantageously, the use of a locking mechanism may allow, for example, the sensors to maintain a fixed position so that properties such as, for example, the water level of the body of water to be more accurately measured. The locking mechanism, when present, may be of any suitable form. Preferably, the attachment means of the water monitoring device may be adapted to comprise the further locking mechanism, when present. In certain embodiments, the locking mechanism may be in the form of a threaded region operable to threadedly engage with a threaded region of a water inlet and/or water outlet. It will be appreciated by a person skilled in the art that when this form is employed the attachment means and the locking means may be the same.

The treatment members of the apparatus and/or kits of parts of the present invention may also comprise communication members. The communication member(s) of the water monitoring device, and optionally of the treatment member(s), may be operable to transmit and/or receive data to a remote device, and optionally to the water monitoring device and/or other treatment members. The data may be transmitted from the communication member by any suitable method, which will be well known to the person skilled in the art. Preferably, the data is communicated wirelessly. For example, the data may be transmitted by radio signal, such as Bluetooth™, a wireless local area network, a cellular network or a combination thereof.

The data may be transmitted from the communication member in any suitable form. For example, the data may be transmitted in the format of a text message, or an email. The data may be transmitted from the communication member directly or indirectly. For example, the data may be transmitted from the communication member directly to the remote device or water monitoring device or may be transmitted via one or more interface devices.

The apparatus and/or kit of parts of the present invention may further comprise a remote device. The remote device may be any suitable device able to receive data from the communication member(s). For example, the remote device may be a computing device such as a desktop computer, a laptop, a tablet computer, a mobile telephone, including, for example, smart phones, and the like. Preferably, the remote device is a hand-held device. For example, the remote device may be a hand-held device such as a mobile telephone including, for example, smart phones or a tablet computer. The remote device may comprise a user interface (UI). Suitably, the UI may be operable to allow the user to view the transmitted data, manipulate the transmitted data, input parameters, such as those relating to one or more properties of the body of water, send instructions to the water monitoring device, or treatment member of the apparatus. In this way, advantageously, a user may be able to easily view and manipulate the data transmitted from the communication member(s). The UI may optionally comprise an alarm function. Suitably, the UI may comprise an alarm function operable to alert the user when a detected property of the body of water is non-optimal. By the term "non-optimal" and like terms as used herein is meant that a particular property of the body of water, such as a swimming pool, falls outside of a range which is suitable for use. The suitable ranges may be set manually by the user or may be set automatically, such as by being pre-programmed into the device. For example, the alarm may be operable to alert the user when the temperature of the body of water, such as a swimming pool, is too high or too low or when the chlorine levels of the body of water, such as a swimming pool, are too high or tool low.

Preferably, the water monitoring device and/or remote device comprises a communication member that is operable to transmit data, such as operating instructions, to one or more of the treatment members. For example, the water monitoring device and/or remote device may be operable to transmit data to treatment devices operable to control one or more of a light source; chemical levels, such as chlorine level and/or pH; temperature; robotic cleaner, ozone generator, water cover, pump or filter. Advantageously, the user may effect changes in the operation of the treatment members remotely by direct communication with the treatment members or via the water monitoring device in response to the data provided by the water monitoring device.

Advantageously, the present invention reduces the risk of the body of water, such as a swimming pool, from developing poor water conditions, such as, for example, reducing or substantially preventing the risk of the body of water from developing algae and harmful bacteria.

Preferably the water monitoring device and/or the remote device is operable to transmit data to a robotic cleaner and/or receive data from a robotic cleaner. For example, the water monitoring device and/or remote device may be operable to transmit data regarding its location to a robotic cleaner, may receive data regarding the location of the robotic cleaner within the body of water, the power status of the robotic cleaner and/or send instructions as to the cleaning cycle to be initiated. Suitably, the data received from and/or sent to the water monitoring device would be available to the user in real time via the remote device. The cleaning parameters may be predetermined or may be manipulated by user, for example, via the UI as hereinbefore described.

Preferably, the apparatus and/or kit of parts of the present invention comprises a robotic cleaner operable to communicate with the water monitoring device and/or the remote device.

Advantageously, when the cleaning cycle is controlled remotely by the user the cleaning operation may be optimized for different types of cleaning and/or different contaminations. For example, the cleaning operation may be optimized in response to real time data regarding one or more properties of the body of water, such as a swimming pool.

The water monitoring device, assembly, apparatus and/or kit of parts of the present invention may further comprise a docking station for a robotic cleaner. Suitably, the docking station may be operable to charge and/or exchange data with a robotic cleaner. The robotic cleaner may be operable to receive data regarding the location of the docking station of the water monitoring device and to manoeuvre itself to or from the docking station. The docking station, when present, may be located at any suitable location. For example, the docking station, when present, may be arranged on the water monitoring device. The robotic cleaner may comprise a battery. Optionally, the cleaner may comprise traction motors, controllers and/or vacuum filter motors. The docking station may be operable to recharge the battery of the cleaner preferably such that components of the cleaner including traction motors, controllers, and/or vacuum filter motors are able to operate. Suitably, the docking station and cleaner comprise inductive members operable to allow for contactless charging and/or data transfer when the robotic cleaner is in proximity to this monitoring device.

The water monitoring device and/or the robotic cleaner may comprise one or more sensors operable to generate data in relation to the location of the robotic cleaner/device, preferably the device and/or cleaner comprises two or more spaced sensors operable to generate date in relation to the location of the device/cleaner. Suitably, the sensors are arranged on the device and/or robotic cleaner such that data may be obtained that allows the performance of triangulation position locating calculations to determine the location of the cleaner in the pool and/or relative to the device. In this way, advantageously the use of multiple of sensors allow for more accurate data to be generated in relation to the location of the device/cleaner. The sensor(s) for determining the location of the device/cleaner may comprise a laser, hydrosonic, radiowave, and/or ultrasonic transmitting and receiving sensor, suitably the sensor comprises means to collect reflected laser light, radiowaves and/or sound waves. Optionally, the device and/or cleaner may comprise optical sensors. Optionally, the cleaner does not comprise means to determine its location within the body of water and/or relative to the device, preferably the water monitoring device and/or remote device is operable to determine the location of the cleaner using the data obtained and is operable to transmit instructions to the cleaner. Advantageously, the substantially fixed position of the water monitoring device provides the robotic cleaner with a set point of reference from which data can be generated in relation to its position at any one time.

The water monitoring device, robotic cleaner and/or remote device may be operable to calculate the route taken by the robotic cleaner and/or calculate the route to be taken by the cleaner. For example, the water monitoring device may be operable to transmit data relating to the route that the robotic cleaner should take around the body of water. In this way, advantageously, the robotic cleaner may avoid cleaning the same area of the body of water more than once and/or may focus on parts of the body of water that have been missed.

Advantageously, use of a robotic cleaner controlled by a water monitoring device or apparatus according to any aspect of the present invention allows for a more energy efficient cleaning cycle, for example, by enabling the robotic cleaner to follow a more efficient route. It also enables recharging of the cleaner without removal of the cleaner from the body of water.

The device, assembly, apparatus and/or kits of parts according to any aspect of the present invention may further comprise a power source. Suitably, the power source may comprise an electrical power source. Preferably, the power source may comprise a battery or a solar power source.

In certain embodiments, a battery, when present, may be removable for charging. A battery may be chargeable by inductive charging means, pulse charging means or solar charging means. In certain embodiments, a battery, may be chargeable by inductive charging means. Accordingly, the apparatus or kit of parts according to the present invention may optionally further comprises a charging unit operable to inductively charge the device or assembly. Advantageously, the use of inductive charging means allows for a contactless inductive power transfer to charge the battery, allowing for a more watertight construction.

Preferably, data may be transmitted to and/or from the water monitoring device via the inductive charging means.

In certain embodiments, a battery, may be chargeable by pulse charging means. Accordingly, the apparatus or kit of parts according to the present invention may optionally further comprises a unit operable to pulse charge the water monitoring device or assembly. Preferably, the unit operable to pulse charge the water monitoring device may use a flow detection mechanism, or the like, to pulse charge the battery.

In certain embodiments, a solar power source, when present, may be attached to or may be integral with the attachment means of the device or assembly.

The water monitoring device according to any aspect of the present invention may further comprise a generator operable to generate power for use by the water monitoring device. The generator may comprise a turbine assembly arranged and operable to generate electricity when water flows through the turbine, suitably as water flows through a water inlet and/or water outlet of the body of water. Preferably, the generator is removably attachable to the water monitoring device. In such a scenario, the water monitoring device may be operable to draw power from the generator by means of a plug and socket arrangement, which may be via inductive coupling, for example, or by other means of charge transfer. The water monitoring device may be secured to the generator via securing means, such as clips, for example.

The water monitoring device according to any aspect of the present invention may further comprise switching means. Suitably, the switching means may be operable to switch the or each electrically powered device between an on and off position. The switching means may one or more comprise manual switches. The switching means may operate remotely, for example by operation of a remote control unit and/or the remote device as hereinbefore described.

The switching means may comprise a timer which may independently allow the or each electrically powered device to be switched on or off at a predetermined time. The timer may be programmable, for example, a remote control unit and/or the remote device as hereinbefore described.

Suitably, the water monitoring device may comprise a housing in which one or more of the other components of the water monitoring device may be located. Preferably, the housing is formed from plastic, more preferably the housing provides a watertight seal around an interior cavity.

Any suitable number of water monitoring devices according to any aspect of the present invention may be fitted to a body of water, such as a swimming pool. The water monitoring devices may be fitted to one or more water inlets, one or more water outlets or a combination thereof. Advantageously, the use multiple water monitoring devices may allow for more properties of the body of water to be detected and/or more data points to be collected. This would allow for more comprehensive data processing to allow for improved parameter manipulation and system effectiveness.

For the avoidance of doubt, by the term "body of water" and like terms as used herein is meant the volume of water within the system and includes water present in the main body of water and in the water inlet and/or water outlet. For the avoidance of doubt, by the term "main body of water" and like terms as used herein is meant the bulk of the water present in the system and excludes the water present in the water inlet and/or water outlet. For example, when the body of water is a swimming pool, the main body of water is that located within the space defined by the side walls and the bottom floor of the pool, excluding the water present in any water inlets and/or water outlets. For the avoidance of doubt, by the term "water inlet and/or water outlet" it is meant any means by which water may flow into (i.e. water inlet) and/or out of (i.e. water outlet) the main body of water. For example, the water inlet and/or outlet may be a channel or a pipe that allows water to flow into and/or out of the main body of water. It will be appreciated by a person skilled in the art that a water inlet may also act as a water outlet and vice versa. The water inlet and/or water outlet may project into or out of the body of water. For example, the water outlet may be a fountain head.

All of the features contained herein may be combined with any of the above aspects in any combination.

BRIEF DESCRIPTION OF THE DRAWINGS

For a better understanding of the invention, and to show how embodiments of the same may be carried into effect, reference will now be made, by way of example, to the following figures.

DETAILED DESCRIPTION OF THE DRAWINGS

Figure 1:
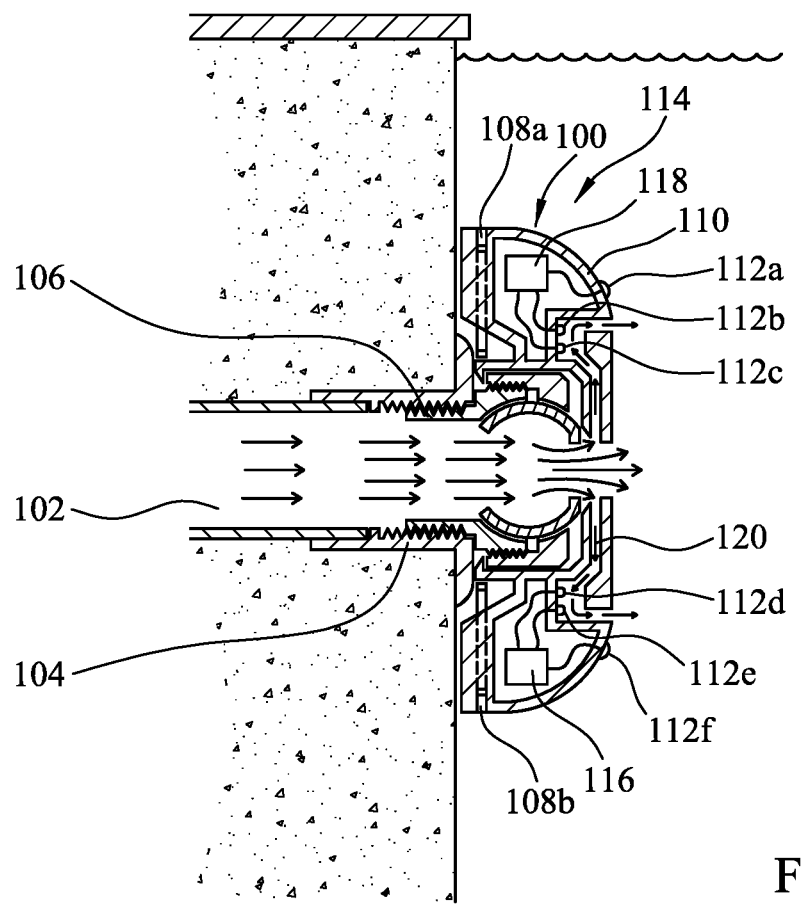
FIG. 1 shows a schematic representation of a water monitoring device according to a first embodiment of the present invention arranged in a swimming pool.

FIG. 1 shows a water monitoring device (100) removably attached adjacent to a water inlet (102) of a swimming pool. The water inlet (102) has a threaded section (104) which is threadedly engaged with a corresponding threaded section (106) on the water monitoring device (100) such that the water monitoring device (100) is held in a substantially stationary position adjacent to the water inlet (102). The water monitoring device (100) has a housing (110) formed from plastic. The water monitoring device (100) has six sensors (112a-t); two of which (112a, 112f) are located on the outside of the housing (110) in the main body of water (114) of the swimming pool and four of which (112b, 112c, 112d, 112e) are located on the inside of the housing (110) adjacent to the water inlet (102). The water monitoring device (100) includes a battery (116). The battery (116) is removable for, for example, charging or replacement. The water monitoring device (100) also includes electronics (118), powered by the battery (116), that are operable to run the sensors (112a-t). The electronics (118) are protected from water damage by the housing (110). In use, the water monitoring device (100) detects properties of the water in the swimming pool using the sensors (112a-t). The sensors (112a, 112f) located on the outside of the housing (110) detect properties of the main body of water (114) in the swimming pool. The sensors (112b, 112c, 112d, 112e) located on the inside of the housing (110) detect properties of the water in the flow of the water inlet (120).

Figure 2:
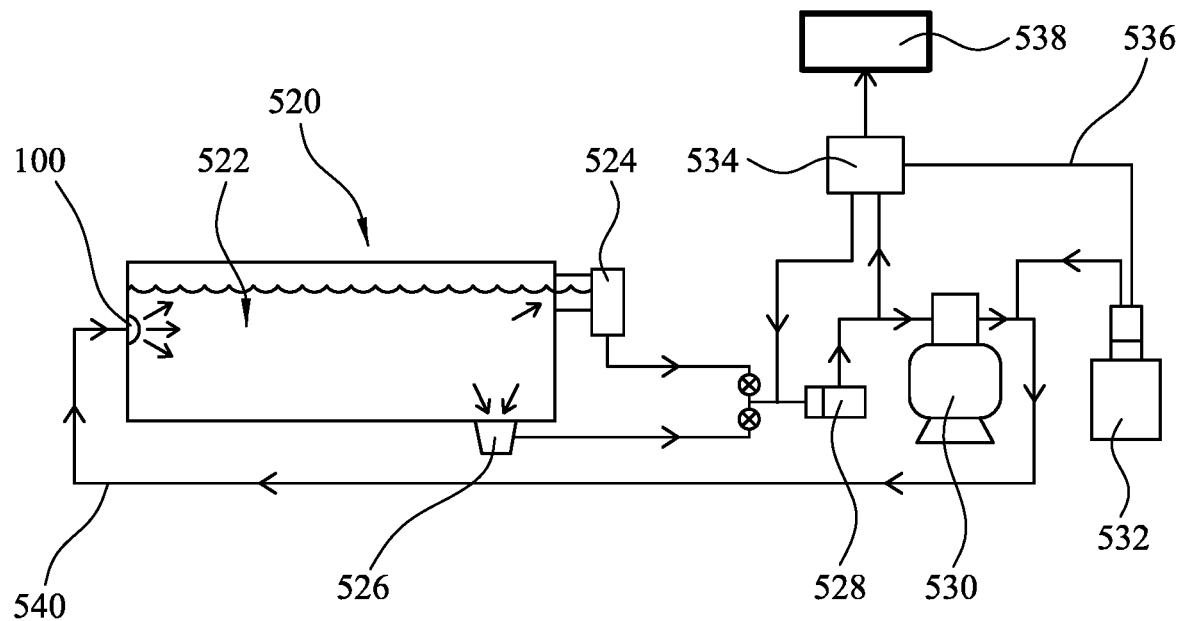
FIG. 2 shows a schematic representation of a water management apparatus according to a second embodiment of the present invention containing the device of FIG. 1.

FIG. 2 shows a water management apparatus (520) arranged about a pool (522). The apparatus (520) is formed of a surface skimmer (524), a sump (526), a filter circulating pump (528), a sand filter (530), a chemical dosing system (532), a chemical controller (534), a dosing system power supply and data connection (536), receiver and transmitter (538), filtered water return (540) and water monitoring device (100). The communication member of device (100) is operable to send instructions to the receiver (538) to increase or decrease the chemical release of dosing system (532).

In use, water from the pool passes into the surface skimmer (524) or the sump (526). It is then filtered by the sand filer (530) after which an appropriate amount of chemicals, such as chlorine, are added to the water. The amount added by chemical dosing system (532) is determined by the chemical controller (534). The filtered and treated water is then returned to the pool via the filtered water return (540) and water monitoring device (100).

Figure 3:
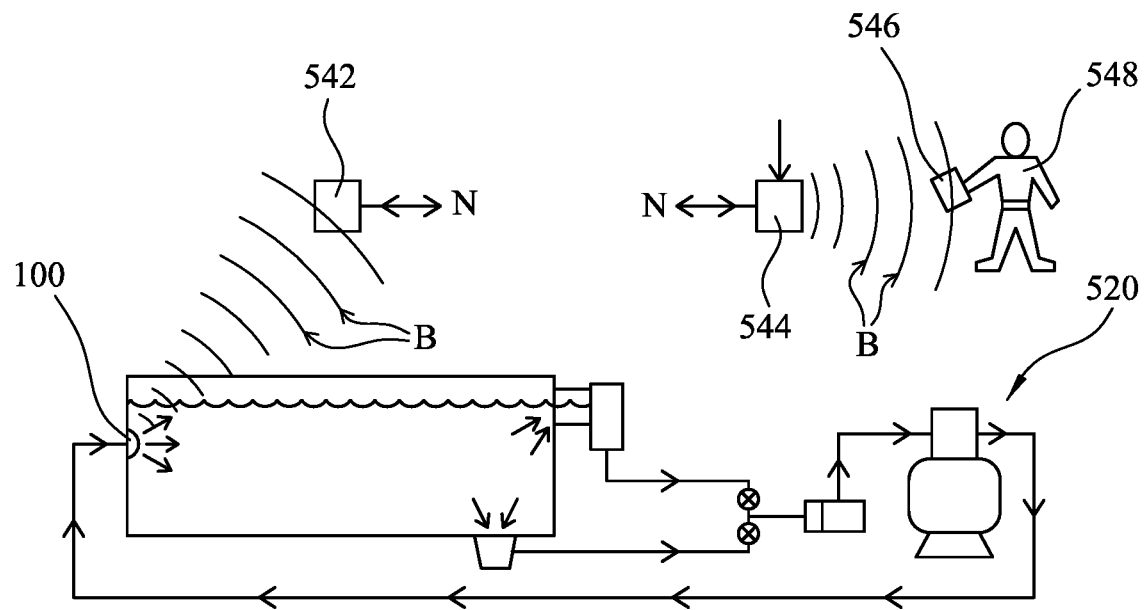
FIG. 3 shows a schematic representation of the water management apparatus according to FIG. 2.

FIG. 3 shows the communication system of water management apparatus (520). The communication system is formed of transmitter (not shown) in device (100), an interface module (542) a wireless interface module (544) and a remote mobile telephone device (546). In use, the transmitter sends data relating to a property of the pool water to module (542) over radio waves (B). Module (542) then sends the data over a wireless network (N) to module (544) which then transmits the data to device (546). The user (548) may then view the data on the mobile device (546). Optionally, device (100) or controller (534) may comprise a receiver such that instructions may be sent from device (546) to device (100) or controller (534). In another embodiment, device (100) may transmit data directly to device (546).

Figure 4:
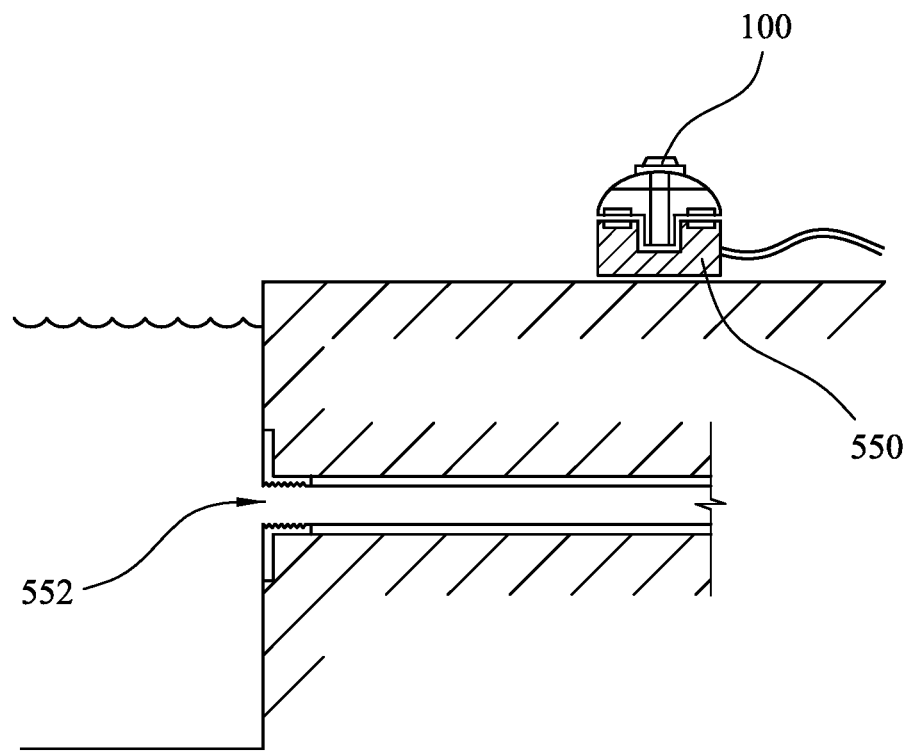
FIG. 4 shows a schematic representation of the water monitoring device of FIG. 1 arranged on a charging member.

FIG. 4 shows water monitoring device (100) arranged in inductive charging station (550). Device (100) has been removed from pool outlet (552) and contacted with charging station (550) on the pool deck. When in contact as in FIG. 4, device (100) comprises receiving coils that contact charging coils in station (55).

Figure 5:
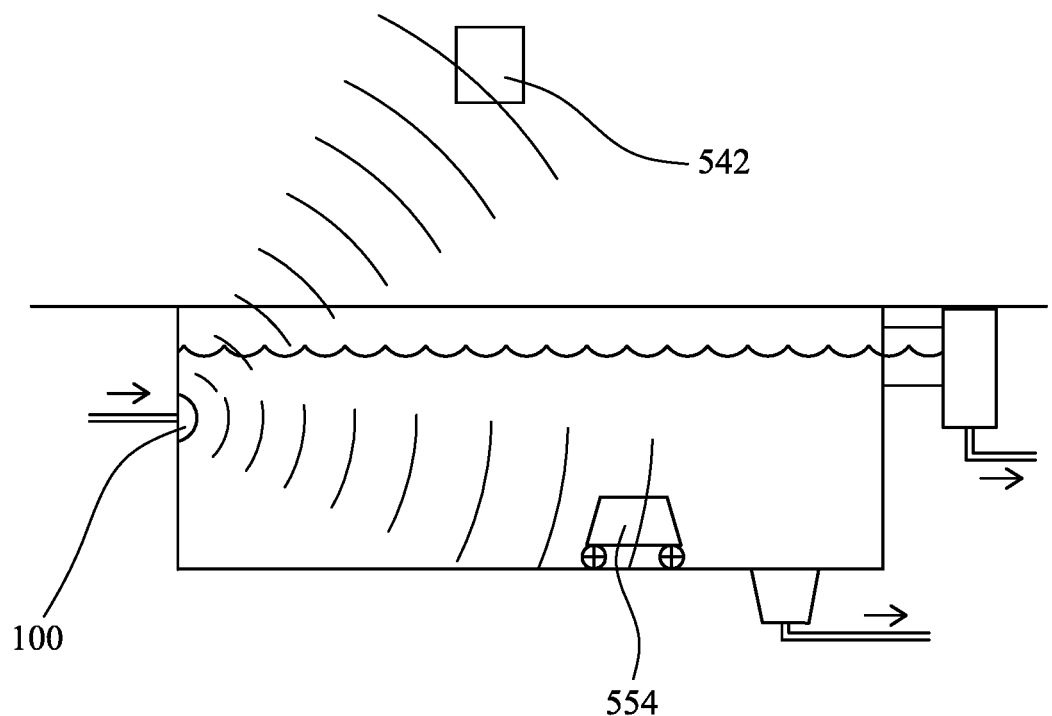
FIG. 5 shows a schematic representation of the water managing apparatus according to FIG. 2 and a robot cleaner.

FIG. 5 shows water monitoring device (100) interacting with robotic cleaner (554). The water monitoring device is able to determine the location the cleaner (554) and the route that it has taken around the pool. Device (100) can transmit this data to mobile device (546). Device (100) can recommend a route for the cleaner (554) during a cleaning cycle or the user may input a route from device (546).

Figure 6:
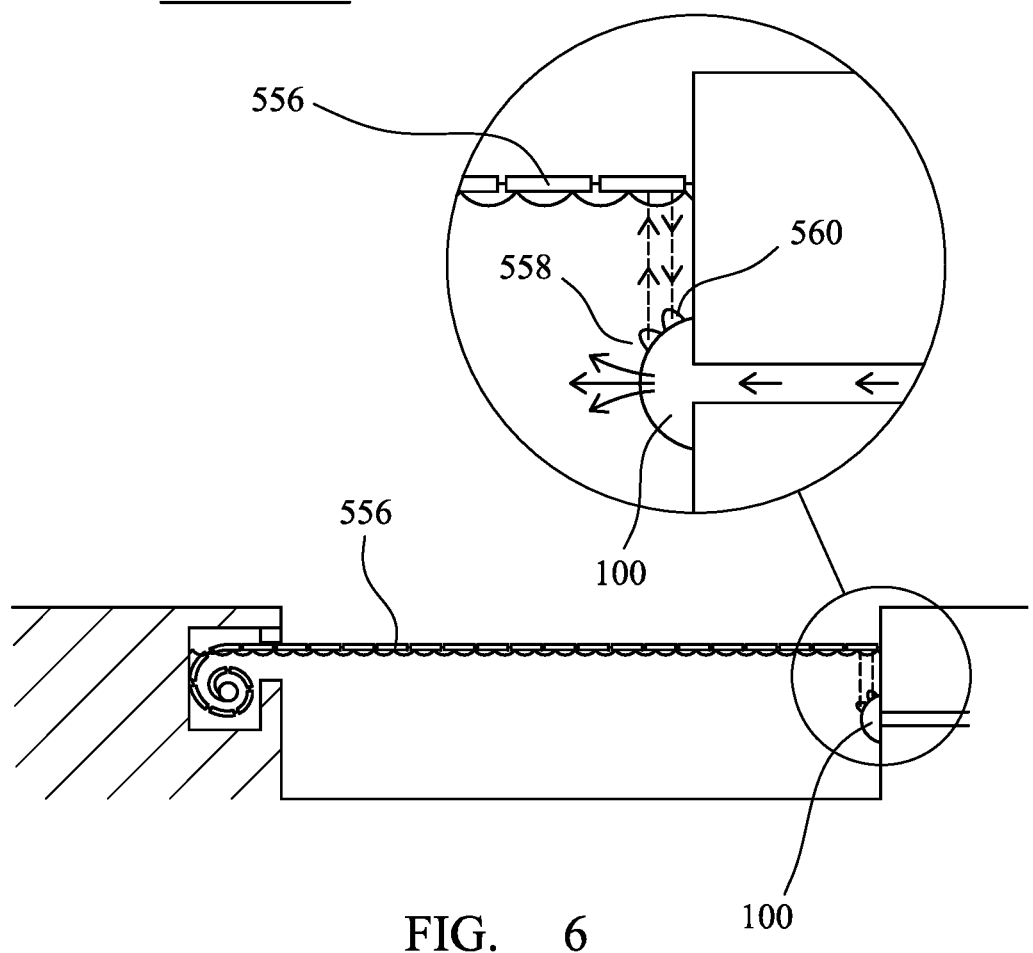
FIG. 6 shows a schematic representation of the water monitoring device of FIG. 1 arranged in a swimming pool having a pool cover.

FIG. 6 shows water monitoring device (100) arranged in a pool having a pool cover (556) extending over the surface of the water. Device (100) has light transmitter (558) and light receiver (560). The transmitter (558) sends light toward cover (556) and light reflected back from the cover (556) toward device (100) is collected by receiver (560). Device (100) can then determine if cover (556) is correctly in place over the pool.

Figure 7:
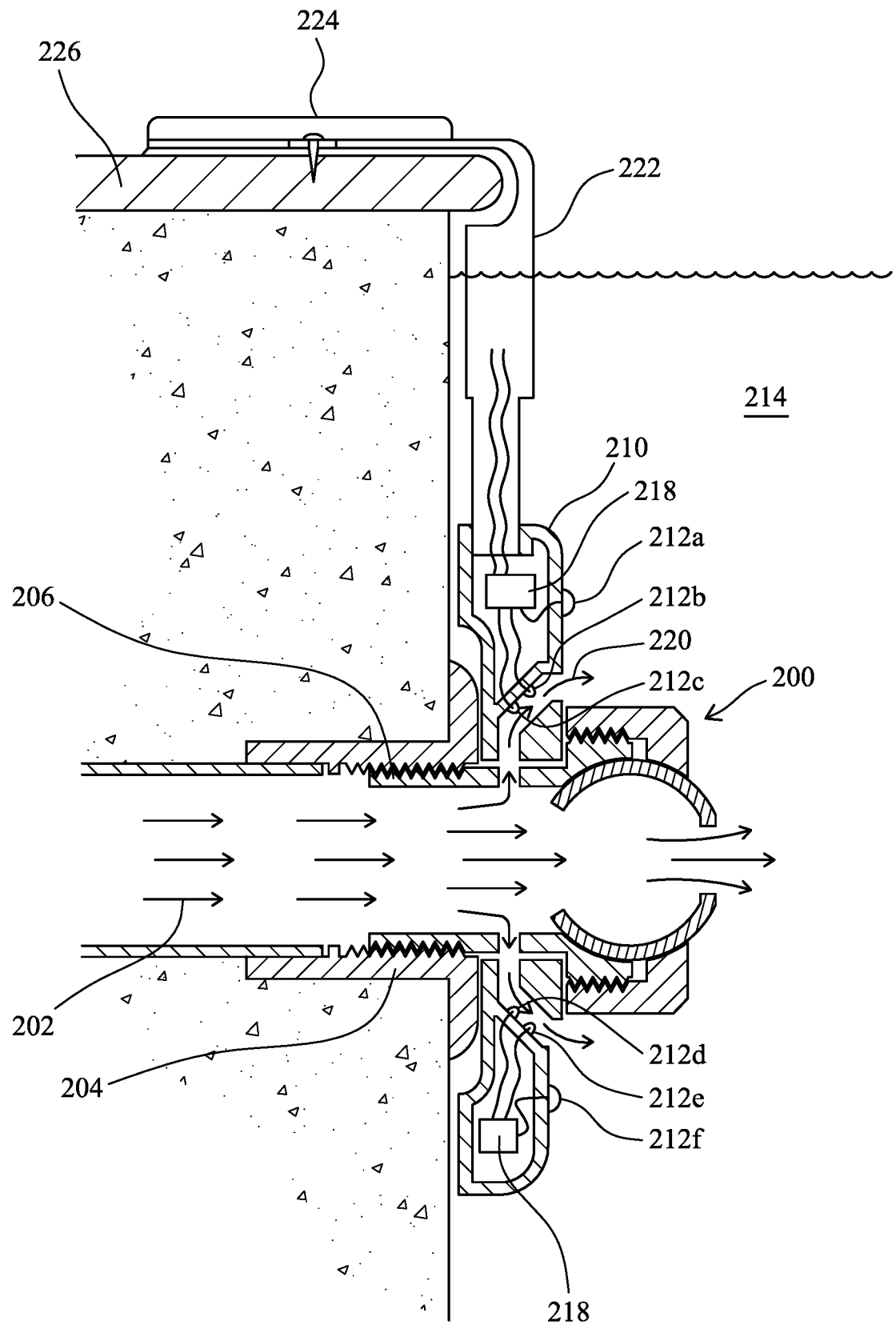
FIG. 7 shows a schematic representation of a second embodiment of a water monitoring device according to the present invention.

FIG. 7, in which like features to the embodiment of FIG. 1 are shown with the same reference numerals as FIG. 1 except that the first number '1' has been replaced with a '2', shows a water monitoring device (200) according to a further exemplary embodiment of the present invention. The water monitoring device (200) is removably attached adjacent to a water inlet (202) of a swimming pool. The water inlet (202) has a threaded section (204) which is threadedly engaged with a corresponding threaded section (206) on the water monitoring device (200) such that the water monitoring device (200) is held in a substantially stationary position adjacent to the water inlet (202). The water monitoring device (200) is further held in place by a member (222) attached to a solar panel (224) located on the top of the side wall (226) of the swimming pool. Optionally, device (200) may be held in position adjacent to inlet/outlet only by solar panel (224) and the connection thereto. The water monitoring device (200) has a housing (210) formed from plastic. The water monitoring device (200) has six sensors (212a-t); two of which (212a, 212f) are located on the outside of the housing (210) in the main body of water (214) of the swimming pool and four of which (212b, 212c, 212d, 212e) are located on the inside of the housing (210) adjacent to the water inlet (202). The water monitoring device (200) also includes electronics (218), powered by the solar panel (224), that are operable to run the sensors (212a-t). The electronics (218) are protected from water damage by the housing (210). In use, the water monitoring device (200) detects properties of the water in the swimming pool using the sensors (212a-t). The sensors (212a, 212f) located on the outside of the housing (210) detect properties of the main body of water (214) in the swimming pool. The sensors (212b, 212c, 212d, 212e) located on the inside of the housing (210) detect properties of the water in the flow of the water inlet (220). The solar panel (224) has an integrated communication member (not shown) which as able to transmit data to and receive data from a remote device (not shown). The communication device (not shown) is powered by the solar panel (224).

Figure 8:
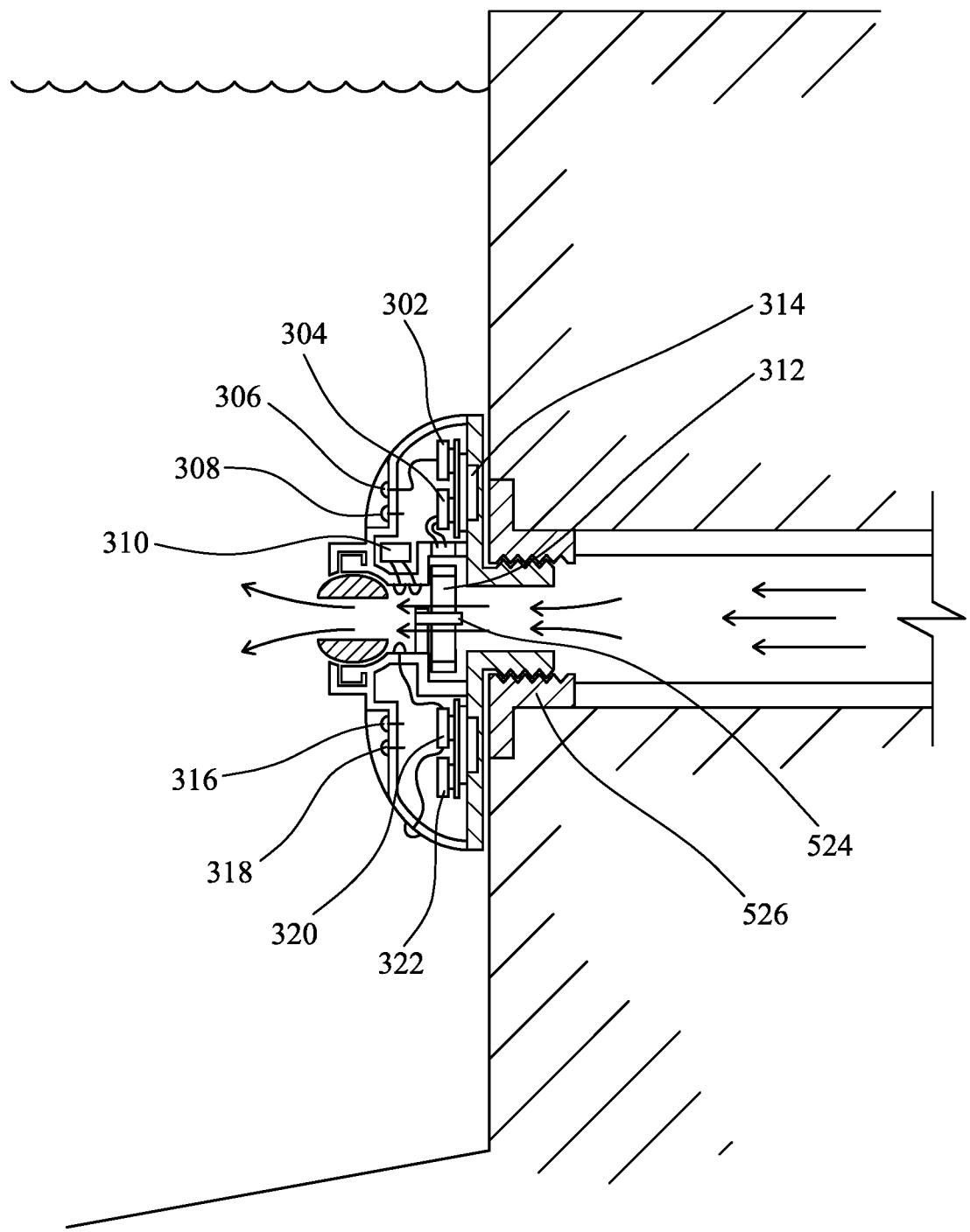
FIG. 8 shows a schematic representation of a third embodiment of a water monitoring device according to the present invention.

FIG. 8 shows a third embodiment of a water monitoring device (300) according to the present invention. Device (300) is arranged in water return outlet (526) and is formed of transmitter and receiver control module (302); connected to signal receiver and transmitter antenna (306); charging module (304); inductive charging receiving coils (314); battery module (322); LED indicators (308); chemical analyser module (310) for determining chlorine and pH levels; flow detection blades (312) arranged on spindle (524); occupancy detector (316); camera (318); temperature module (320) with main body and outlet channel probes.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A water monitoring device for monitoring a body of water in a swimming pool, the body of water comprising a main body of water in the swimming pool and a water inlet and/or water outlet to/from the main body of water, the water monitoring device comprising:
    a first sensor operable to generate data in relation to a property of the main body of water and a second sensor operable to generate data in relation to a property of the water at the inlet and/or outlet;
    an attachment member operable to removably arrange the device in a stationary position adjacent to the water inlet and/or water outlet of the body of water; and
    a communication member operable to transmit the data relating to a property of the body of water to a remote device;
and wherein the first and second sensor are operable to generate data in relation to a same property.

2. A water monitoring device according to claim 1, wherein the sensor is operable to detect chemical levels in the body of water, a chlorine content, the pH, a mineral content, a presence of microorganisms; or a combination thereof, and/or the sensor is operable to detect physical aspects of the body of water, the temperature of the water; the water level; a flow speed; clarity of the water; or a combination thereof and/or the sensor is operable to directly detect the performance of treatment members.

3. A water monitoring device according to claim 1, wherein the sensor comprises an optical transmitter and receiver.

4. A water management apparatus for monitoring and managing properties of a body of water comprising a main body of water and a water inlet and/or water outlet, the water management apparatus comprising:
    a water monitoring device according to claim 1; and
    at least one treatment member operable to effect a change in a property of the body of water.

5. A water monitoring device according to any of claim 4, wherein the apparatus comprises a robotic cleaner operable to communicate with the water monitoring device.

6. A water monitoring device according to claim 1, wherein a treatment member is selected from the group consisting of a heater, a water heating element; a chemical dosing member, salt generator, a chlorinator; an ionizer; a water cooling element; a hydro-sonic device; a laser light projecting device; an ozone generator; an audible alarm, a pump, a filter, a cover, a robotic cleaner and combinations thereof.

7. A water monitoring device according to claim 1, and further comprising a hand-held device.

8. A water monitoring device according to claim 1, wherein at least one treatment member comprises a communication member operable to transmit and/or receive data to a remote device and/or to the water monitoring device and/or other treatment members.

9. A water monitoring device according to claim 1, wherein the water monitoring device and/or remote device comprises a communication member that is operable to transmit data to one or more treatment members.

10. A water monitoring device according to claim 1 wherein the remote device comprises a user interface (UI) operable to allow a user to view the transmitted data, manipulate the transmitted data, input parameters, and send instructions to the water monitoring device and/or a treatment member.

11. A water monitoring device according to claim 1, and further comprising a docking station for a robotic cleaner.

12. A water monitoring device according to claim 11, wherein the docking station and robotic cleaner comprise inductive members operable to allow for contactless charging and/or data transfer when the robotic cleaner is in proximity to the monitoring device.

13. A water monitoring device according to claim 1, wherein the water monitoring device comprises one or more sensors operable to generate data in relation to the location of the water monitoring device.

14. A water monitoring device according to claim 1, wherein the water monitoring device, robotic cleaner and/or remote device is operable to calculate a route taken by the robotic cleaner and/or calculate the route to be taken by the robotic cleaner, wherein the water monitoring device is operable to transmit data relating to the route that the robotic cleaner should take around the body of water.

15. A water monitoring device or apparatus according to claim 1, further comprising a power source, selected from the group consisting of a battery and a solar power source.

16. A water monitoring device or apparatus according to claim 1, further comprising a charging unit operable to inductively charge the device or assembly.

17. A water monitoring device according to claim 16, wherein data can be transmitted to and/or from the water monitoring device via the inductive charging unit.

18. A method of monitoring a body of water in a swimming pool, and managing a property of the body of water, the body of water comprising a main body of water in the swimming pool and a water inlet and/or water outlet to/from the main body of water, the method comprising:
    attaching a water monitoring device according to claim 1 in a stationary position adjacent to the water inlet and/or water outlet of the body of water;
    generating data from a first sensor in relation to a property of the main body of water and generating data from a second sensor in relation to a property of the water at the inlet and/or outlet;

communicating the data to a remote device; and
sending an instruction from the remote device to a water treatment member that is operable to effect a change in a property of the body of water.

\* \* \* \* \*